United States Patent [19]

Rebafka

[11] Patent Number: 4,762,929

[45] Date of Patent: Aug. 9, 1988

[54] AROMATIZATION OF SATURATED NITROGEN-CONTAINING HETEROCYCLES

[75] Inventor: Walter Rebafka, Hirschberg, Fed. Rep. of Germany

[73] Assignee: BASF Aktiengesellschaft, Fed. Rep. of Germany

[21] Appl. No.: 58,622

[22] Filed: Jun. 4, 1987

Related U.S. Application Data

[63] Continuation of Ser. No. 713,643, Mar. 19, 1985, abandoned.

[30] Foreign Application Priority Data

Mar. 22, 1984 [DE] Fed. Rep. of Germany ....... 3410542

[51] Int. Cl.⁴ ............... C07D 213/133; C07D 207/32; C07D 241/12
[52] U.S. Cl. .................... 546/252; 548/564; 544/410
[58] Field of Search .............. 548/564; 544/410; 546/252

[56] References Cited

U.S. PATENT DOCUMENTS

| 4,118,400 | 10/1978 | Michaely | 549/434 |
| 4,401,819 | 8/1983 | Cordier et al. | 546/252 |

FOREIGN PATENT DOCUMENTS

| 653723 | 12/1962 | Canada | 548/564 |
| 67360 | 12/1982 | European Pat. Off. | 548/564 |
| 1192648 | 1/1966 | Fed. Rep. of Germany . | |
| 3123302 | 5/1983 | Fed. Rep. of Germany . | |
| 60-169468 | 9/1985 | Japan | 544/410 |
| 1393088 | 5/1975 | United Kingdom . | |

OTHER PUBLICATIONS

Takahashi et al., Chem. Abstracts, vol. 88, (1978), entry 190350b.

*Primary Examiner*—Donald G. Daus
*Assistant Examiner*—William A. Teoli, Jr.
*Attorney, Agent, or Firm*—Keil & Weinkauf

[57] ABSTRACT

Saturated nitrogen-containing five-membered and six-membered heterocycles are aromatized by dehydrogenation in the gas phase in the presence of a supported palladium catalyst containing an alkaline earth metal halide, at from 150° to 350° C. and under from 0.1 to 10 bar.

9 Claims, No Drawings

AROMATIZATION OF SATURATED NITROGEN-CONTAINING HETEROCYCLES

This application is a continuation of application Ser. No. 713,643, filed on Mar. 19, 1985, now abandoned.

The present invention relates to a novel process for the aromatization of saturated nitrogen-containing five-membered and six-membered heterocycles by dehydrogenation in the presence of a palladium catalyst which contains an alkaline earth metal halide.

It is known that piperidine can be converted to pyridine by dehydrogenation. DE-B-No. 1 192 648 proposes carrying out this reaction by means of a supported catalyst comprising a silica gel carrier and palladium or platinum as the active component in the presence of hydrogen. In this process, however, the space velocity is 0.013 l of piperidine per l of catalyst per hour, which is much too low. Moreover, the catalyst life is unsatisfactory, the amount of pyridine discharged falling from 80% to 54% after only 16 days.

In GB-A-No. 1 399 088, this reaction is carried out over a palladium/silica gel catalyst. In this procedure, however, only special palladium compounds which are soluble in acetic acid can be used for impregnating the silica gel, and the subsequent activation of the catalyst is very complicated. In this process, too, the catalyst life is poor, as confirmed by the deactivation rates.

Finally, EP-A-No. 61 982 describes a process for the dehydrogenation of unsubstituted or alkyl-substituted piperidine to the particular pyridine, supported palladium catalysts being used. The silica gel carrier has to meet stringent requirements with regard to particle size and pore volume. Furthermore, according to Example 1, the productivity of β-picoline decreases to 25% of the initial value in the course of 13 days.

The dehydrogenation of pyrrolidines to the corresponding pyrroles is also known. For example, DE-A-No. 3 123 202 proposes carrying out the reaction with supported palladium catalysts which contain basic compounds and/or elements of group 1B, 2B or 7B, cobalt and/or nickel. In this process, too, the space velocity is much too low (0.08 l of pyrrolidine per l of catalyst per hour).

Furthermore, a common disadvantage of all of the processes discussed is that, in order to reduce the catalyst or to increase or maintain the activity, the dehydrogenation is carried out in the presence of additional hydrogen. The molar ratios are as follows 6 moles of hydrogen per mole of piperidine in DE-B-No. 1 192 648, 10 moles of hydrogen per mole of piperidine in GB-A-No. 1 393 087, 3 moles of hydrogen per mole of 3-methylpiperidine in EP-A-No. 61 982 and 2 moles of hydrogen per mole of pyrrolidine in DE-A-No. 3 123 302.

These amounts of hydrogen used in addition (to the hydrogen formed during the dehydrogenation) make the process technically more complicated to carry out. This is evident, for example, from the fact that hydrogen has to be provided, recycle gas pumps have to be installed and operated, additional amounts of energy are required for heating the hydrogen to the particular reaction temperature, and additional measures have to be taken for condensing the reacted mixture.

It is an object of the present invention to provide a process which makes it possible to dehydrogenate nitrogen-containing heterocycles without having to accept the disadvantages described.

I have found that this object is achieved, and that saturated nitrogen-containing five-membered and six-membered heterocycles can advantageously be aromatized by dehydrogenation in the gas phase, if the dehydrogenation is carried out in the presence of a supported palladium catalyst containing an alkaline earth metal halide, at from 150° to 350° C. and under from 0.1 to 10 bar.

For the purposes of the present invention, aromatization is the complete dehydrogenation of the nitrogen-containing heterocycles to give cyclic systems containing 6 electrons. In conformity with the Huckel rule, such systems possess aromatic properties.

Saturated nitrogen-containing five-membered and six-membered heterocycles which can be used as starting materials in the novel process are tetrahydrazoles and -diazoles and hexahydroazines and -diazines.

Examples of five-membered rings are, in particular, pyrrolidine and its alkyl-substituted derivatives, eg. N-methylpyrrolidine or 3-ethylpyrrolidine.

Examples of six-membered rings are, in particular, piperidine and its alkyl-substituted derivatives, eg. 3-methylpiperidine or 4-methylpiperidine, and piperazine and its alkyl-substituted derivatives, eg. 2-methylpiperazine or 2,3-dimethylpiperazine.

The dehydrogenation is carried out in the gas phase by a continuous procedure. According to the invention, the reaction is carried out at from 150° to 350° C., preferably from 200° to 300° C., and under from 0.1 to 10 bar, preferably atmospheric pressure.

The process is effected in a tube reactor using catalyst material in lump form, or in a fluidized bed.

The catalyst used is a supported palladium catalyst which contains an alkaline earth metal halide, preferably an alkaline earth metal chloride. Magnesium chloride or calcium chloride is preferably used, the former being particularly preferred.

The catalyst should contain from 0.1 to 10, preferably from 1 to 5, % by weight, based on the catalyst, of an alkaline earth metal halide.

Its palladium content should be from 0.1 to 10, preferably from 0.25 to 5, % by weight, based on the catalyst.

Suitable carriers are the conventional materials used in catalyst production, e.g. alumina, silica, aluminum silicate, magnesium silicate or active carbon. Alumina is preferably used. The alkaline earth metal halide can be applied in the form of an aqueous solution, together with the appropriate palladium salt solutions, by impregnating the carrier. Separate application of the palladium and the alkaline earth metal halide is also possible.

After the impregnation process, the catalyst is dried, this generally being carried out at from 70° to 200° C., preferably from 100° to 140° C.

The resulting catalyst is ready-to-use and does not need to be activated by means of hydrogen gas, as is required in general in the prior art processes.

The fact that the presence of additional hydrogen can be dispensed with when carrying out the novel process is also particularly advantageous.

Using the novel process, it is possible to dehydrogenate the stated heterocycles at a space velocity of $\geq 0.2$ l of substrate per l of catalyst per hour, in the absence of hydrogen as a reaction gas or carrier gas, and with high conversion. The catalyst life is longer than 100 days.

The aromatic nitrogen-containing heterocycles prepared by the novel process are useful intermediates, for example for the preparation of crop protection agents, drugs or dyes.

EXAMPLE

About 200 ml of a catalyst which contained 1% by weight of palladium and 4.5% by weight of magnesium chloride, the percentages in each case being based on the catalyst, and whose carrier consisted of alumina were introduced into a quartz glass tube having a length of 50 cm and a diameter of 2.5 cm.

The reaction tube charged with the catalyst was heated to the particular reaction temperature (cf. Table) by means of an external electric heater. Thereafter, the substrate was introduced continuously into the reaction tube in the gaseous state, the amount of gas fed in per hour being equivalent to the amount of gas produced by vaporization of, in each case, 40 ml of the liquid substrate. The reacted mixture was condensed, and the conversion and selectivity were determined.

TABLE

| Substrate End product | Temperature | Conversion | Selectivity | Operating time |
|---|---|---|---|---|
| N—methylpyrrolidine N—methylpyrrole | 290° C. | 99.5% | 90% | 14 days |
| 3-ethylpyrrolidine 3-ethylpyrrole | 290° C. | 95% | 85% | 14 days |
| piperidine pyridine | 290° C. | 99.5% | 97% | 20 days |
| 3-methylpiperidine 3-methylpyridine | 290° C. | 95% | 93% | 100 days |
| 4-methylpiperidine 4-methylpyridine | 290° C. | 100% | 95% | 4 days |
| 2-methylpiperazine 2-methylpyrazine | 250° C. | 99% | 95% | 10 days |

When each of the experiments was terminated, the catalyst still possessed its full activity.

I claim:

1. In a process for preparing aromatic five- or 6-membered nitrogen-containing heterocycles selected from the group consisting of pyrrols, pyridines and pyrazines, wherein a corresponding saturated heterocycle is contacted with a catalyst in the gas phase, at from 150° to 350° C. and under a pressure of from 0.1 to 10 bar, whereby the saturated heterocycle is dehydrogenated and a corresponding aromatic heterocycle is formed, the improvement which comprises: using as the catalyst a supported palladium catalyst containing an alkaline earth metal halide.

2. The process of claim 1, wherein the alkaline earth metal halide used is an alkaline earth metal chloride.

3. The process of claim 1, wherein the alkaline earth metal halide used is magnesium chloride or calcium chloride.

4. The process of claim 1, wherein the aromatization is carried out at from 200° to 300° C.

5. The process of claim 1, wherein the catalyst contains from 0.1 to 10% by weight, based on its total weight, of an alkaline earth metal halide.

6. The process of claim 1, wherein an alkylpiperidine is dehydrogenated to form the corresponding alkylpyridine.

7. The process of claim 1, wherein methylpiperidine is dehydrogenated to form methylpyridine.

8. The process of claim 1, wherein an alkyl piperidine is dehydrogenated to form the corresponding alkylpyridine, said process taking place without the addition of hydrogen.

9. A process for preparing aromatic five- or 6-membered nitrogen-containing heterocycles selected from the group consisting of pyrrols, pyridines and pyrazines, which comprises: contacting a corresponding saturated heterocycle with a supported palladium catalyst containing an alkaline earth metal halide in the gas phase, at from 150° to 350° C. and under a pressure of from 0.1 to 10 bar, whereby the saturated heterocycle is dehydrogenated and a corresponding aromatic heterocycle is formed, said process taking place without the addition of hydrogen.

* * * * *